(12) United States Patent
Ebright et al.

(10) Patent No.: US 9,187,446 B2
(45) Date of Patent: Nov. 17, 2015

(54) ANTIBACTERIAL AGENTS: SIDECHAINFLUORINATED MYXOPYRONIN DERIVATIVES

(71) Applicant: RUTGERS, THE STATE UNIVERSITY OF NEW JERSEY, New Brunswick, NJ (US)

(72) Inventors: Richard H. Ebright, New Brunswick, NJ (US); Yon W. Ebright, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/386,725

(22) PCT Filed: Mar. 22, 2013

(86) PCT No.: PCT/US2013/033548
§ 371 (c)(1),
(2) Date: Sep. 19, 2014

(87) PCT Pub. No.: WO2013/142812
PCT Pub. Date: Sep. 26, 2013

(65) Prior Publication Data
US 2015/0051275 A1 Feb. 19, 2015

Related U.S. Application Data

(60) Provisional application No. 61/614,387, filed on Mar. 22, 2012.

(51) Int. Cl.
C07D 309/30 (2006.01)
C07D 309/36 (2006.01)

(52) U.S. Cl.
CPC .................... C07D 309/36 (2013.01)

(58) Field of Classification Search
CPC ...................................... C07D 309/36
USPC ........................................ 549/291
See application file for complete search history.

(56) References Cited

U.S. PATENT DOCUMENTS

| 6,022,983 | A  | * | 2/2000 | Wuonola et al. ............... 549/291 |
| 8,114,583 | B2 |   | 2/2012 | Ebright et al. |
| 8,772,332 | B2 |   | 7/2014 | Ebright et al. |
| 2006/0246479 | A1 | * | 11/2006 | Ebright .............. 435/6 |
| 2013/0237595 | A1 |   | 9/2013 | Ebright et al. |
| 2013/0289128 | A1 |   | 10/2013 | Ebright et al. |
| 2013/0296421 | A1 |   | 11/2013 | Ebright et al. |
| 2015/0011647 | A1 |   | 1/2015 | Ebright et al. |
| 2015/0031640 | A1 |   | 1/2015 | Ebright et al. |

FOREIGN PATENT DOCUMENTS

| WO | WO 2007/094799 A1 | 8/2007 |
| WO | WO 2012/037508 A2 | 3/2012 |
| WO | WO 2013/119564 A1 | 8/2013 |
| WO | WO 2013/142812 A1 | 9/2013 |
| WO | WO 2013/192352 A1 | 12/2013 |

OTHER PUBLICATIONS

Belogurov et al., "Transcription inactivation through local refolding of the RNA polymerase structure", Nature 457 (7227), 332-335 (2009).
Chopra, "Bacterial RNA polymerase: a promising target for the discovery of new antimicrobial agents", Curr. Opin. Investig. Drugs 8, 600-607 (2007).
Darst, "New inhibitors targeting bacterial RNA polymerase", Trends Biochem. Sci. 29 (4), 159-162 (2004).
Ho et al., "Structures of RNA polymerase-antibiotic complexes", Curr. Opin. Struct. Biol. 19, 715-723 (2009).
Mukhopadhyay et al., "The RNA Polymerase "Switch Region" is a Target for Inhibitors", Cell 135, 295-307 (2008).
Patent Cooperation Treaty, International Searching Authority, Search Report and Written Opinion for PCT/US2013/033548, 8 pages, Mar. 23, 2013.
Srivastava et al., "New Target for inhibition of bacterial RNA polymerase: switch region", Curr. Opini. Microbiol. 14, 532-563 (2011).
Villain-Guillot et al., "Progress in targeting bacterial transcription", Drug Discov. Today 12 (5/6), 200-208 (2007).

* cited by examiner

Primary Examiner — Nizal Chandrakumar
(74) Attorney, Agent, or Firm — Viksnins Harris & Padys PLLP

(57) ABSTRACT

The invention provides compounds of Formula I:

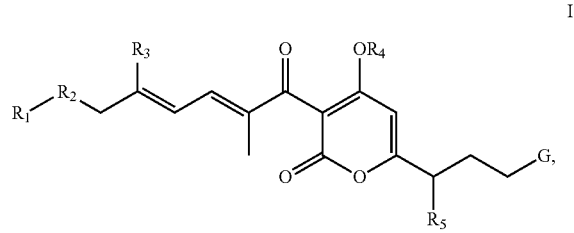

and pharmaceutically acceptable salts thereof, wherein $R^1$, $R^2$, $R^3$, $R^4$, $R^5$, and G are as described in the specification, as well as compositions comprising a compound of formula I, methods of making such compounds, and methods of using such compounds, e.g., as inhibitors of bacterial RNA polymerase and as antibacterial agents.

20 Claims, No Drawings

ANTIBACTERIAL AGENTS: SIDECHAINFLUORINATED MYXOPYRONIN DERIVATIVES

CROSS-REFERENCE TO RELATED APPLICATION(S)

This patent application claims the benefit of priority of U.S. application Ser. No. 61/614,387, filed Mar. 22, 2012, which application is herein incorporated by reference.

STATEMENT OF GOVERNMENT RIGHTS

The invention was made with government support under AI090837 awarded by the National Institutes of Health. The government has certain rights in the invention.

BACKGROUND OF THE INVENTION

Bacterial infectious diseases kill 100,000 persons each year in the US and 11 million persons each year worldwide, representing nearly a fifth of deaths each year worldwide (Heron et al., *Final Data for* 2006. *National Vital Statistics Reports*, Vol. 57 (Centers for Disease Control and Prevention, Atlanta Ga.) and World Health Organization (2008) *The Global Burden of Disease: 2004 Update* (World Health Organization, Geneva)). In the US, hospital-acquired bacterial infections strike 2 million persons each year, resulting in 90,000 deaths and an estimated $30 billion in medical costs (Klevins et al., (2007) Estimating health care-associated infections and deaths in U.S. hospitals. *Public Health Reports,* 122, 160-166; Scott, R. (2009) *The direct medical costs of healthcare-associated infections in U.S. hospitals and benefits of prevention* (Centers for Disease Control and Prevention, Atlanta Ga.)). Worldwide, the bacterial infectious disease tuberculosis kills nearly 2 million persons each year. One third of the world's population currently is infected with tuberculosis, and the World Health Organization projects that there will be nearly 1 billion new infections by 2020, 200 million of which will result in serious illness, and 35 million of which will result in death. Bacterial infectious diseases also are potential instruments of biowarfare and bioterrorism.

For six decades, antibiotics have been a bulwark against bacterial infectious diseases. This bulwark is failing due to the appearance of resistant bacterial strains. For all major bacterial pathogens, strains resistant to at least one current antibiotic have arisen. For several bacterial pathogens, including tuberculosis, strains resistant to all current antibiotics have arisen.

Bacterial RNA polymerase (RNAP) is a proven target for antibacterial therapy (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; Ho, M., Hudson, B., Das, K., Arnold, E., Ebright, R. (2009) *Curr. Opin. Struct. Biol.* 19, 715-723; and Srivastava et al. (2011) *Curr. Opin. Microbiol.* 14, 532-543). The suitability of bacterial RNAP as a target for antibacterial therapy follows from the fact that bacterial RNAP is an essential enzyme (permitting efficacy), the fact that bacterial RNAP subunit sequences are highly conserved (permitting broad-spectrum activity), and the fact that bacterial RNAP-subunit sequences are highly conserved in human RNAP I, RNAP II, and RNAP III (permitting therapeutic selectivity).

The rifamycin antibacterial agents function by binding to and inhibiting bacterial RNAP (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) *Curr. Opin. Struct. Biol.* 19, 715-723). The rifamycins bind to a site on bacterial RNAP adjacent to the RNAP active center and prevent extension of RNA chains beyond a length of 2-3 nt. The rifamycins are in current clinical use in treatment of both Gram-positive and Gram-negative bacterial infections. The rifamycins are of particular importance in treatment of tuberculosis; the rifamycins are first-line antituberculosis agents and are among the few antituberculosis agents able to kill non-replicating tuberculosis bacteria.

The clinical utility of the rifamycin antibacterial agents is threatened by the existence of bacterial strains resistant to rifamycins (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; and Ho, M., Hudson, B., Das, K., Arnold, E., Ebright, R. (2009) Curr. Opin. Struct. Biol. 19, 715-723). Resistance to rifamycins typically involves substitution of residues in or immediately adjacent to the rifamycin binding site on bacterial RNAP—i.e., substitutions that directly decrease binding of rifamycins.

In view of the public-health threat posed by rifamycin-resistant and multidrug-resistant bacterial infections, there is an urgent need for new antibacterial agents that (i) inhibit bacterial RNAP (and thus have the same biochemical effects as rifamycins), but that (ii) inhibit bacterial RNAP through binding sites that do not overlap the rifamycin binding site (and thus do not share cross-resistance with rifamycins.

A new drug target—the "switch region"—within the structure of bacterial RNAP has been identified (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). The switch region is a structural element that mediates conformational changes required for RNAP to bind and retain the DNA template in transcription. The switch region is located at the base of the RNAP active-center cleft and serves as the hinge that mediates opening of the active-center cleft to permit DNA binding and that mediates closing of the active-center cleft to permit DNA retention. The switch region can serve as a binding site for compounds that inhibit bacterial gene expression and kill bacteria. Since the switch region is highly conserved in bacterial species, compounds that bind to the switch region are active against a broad spectrum of bacterial species. Since the switch region does not overlap the rifamycin binding site, compounds that bind to the switch region are not cross-resistant with rifamycins.

It has been shown that the α-pyrone antibiotic myxopyronin (Myx) functions through interactions with the bacterial RNAP switch region (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). Myx binds to the RNAP switch region, traps the RNAP switch region in a single conformational state, and interferes with formation of a catalytically competent transcription initiation complex. Amino acid substitutions within RNAP that confer resistance to Myx occur only within the RNAP switch region. There is no overlap between amino acid substitutions that confer resistance to Myx and amino acid substitutions that confer resistance to rifamycins and, accordingly, there is no cross-resistance between Myx and rifamycins.

A crystal structure of a non-pathogenic bacterial RNAP, *Thermus thermophilus* RNAP, in complex with Myx has been determined, and homology models of pathogenic bacterial RNAP, including *Mycobacterium tuberculosis* RNAP and *Staphylococcus aureus* RNAP, in complex with Myx have been constructed (WO2007/094799; Mukhopadhyay, J. et al. (2008) *Cell.* 135, 295-307; see also Belogurov, G. et al. (2009) *Nature.* 45, 332-335; Ho et al. (2009) *Curr. Opin. Struct. Biol.* 19, 715-723; Srivastava et al. (2011) *Curr. Opin. Microbiol.* 14, 532-543). The crystal structure and homology models define interactions between RNAP and Myx and can be used to understand the roles of the "west" and "east" Myx sidechains as well as the Myx α-pyrone core.

An object of this invention is to provide compounds that have utility as inhibitors of bacterial RNAP.

An object of this invention is to provide compounds that have utility as inhibitors of bacterial growth.

A particular object of this invention is to provide compounds and pharmaceutical compositions that have utility in the treatment of bacterial infection in a mammal.

DETAILED DESCRIPTION OF THE INVENTION

Definitions

The following definitions are used, unless otherwise indicated.

The term "halo" means fluoro, chloro, bromo, or iodo.

The term "alkyl" used alone or as part of a larger moiety, includes both straight and branched chains.

A combination of substituents or variables is permissible only if such a combination results in a stable or chemically feasible compound. The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen atom by a deuterium or tritium, or the replacement of a carbon by a $^{13}$C- or $^{14}$C-enriched carbon are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Antibacterial Agents

The invention provides new compositions of matter that highly potently inhibit bacterial RNA polymerase and inhibit bacterial growth. Compounds of this invention exhibit potencies higher than the potencies of the natural products myxopyronin A and B and of prior-art analogs of myxopyronin A and B.

Compounds of this invention are anticipated to have applications in analysis of RNA polymerase structure and function, control of bacterial gene expression, control of bacterial growth, antibacterial chemistry, antibacterial therapy, and drug discovery.

This invention provides novel compounds that contain alterations of the Myx "west" sidechain that, it is believed, and is shown by Example, have one or more of the following advantages relative to the Myx native "west" side chain: (1) improvement of interactions with the bacterial-RNAP Myx binding site and an adjacent hydrophobic pocket, (2) increased potency of inhibition of bacterial RNAP, (3) increased potency of antibacterial activity, (4) reduction of lipophilicity (lower log D at pH 7.4), (5) reduction of serum protein binding (higher free concentration in the presence of mammalian serum), (6) improvement of metabolic stability (higher stability in the presence of mammalian liver microsomes, in the presence of mammalian liver cells, and upon administration to a mammal), and (7) improvement of antibacterial efficacy upon administration to a mammal.

Said compounds contain an "east" sidechain that, it is believed, may form most or all of the same hydrogen-bonded interactions with the bacterial-RNAP Myx binding site that are formed by the Myx native "east" sidechain.

The compounds of this invention have utility as RNAP inhibitors.

The compounds of this invention have utility as antibacterial agents.

In one aspect, the invention provides a compound of Formula I:

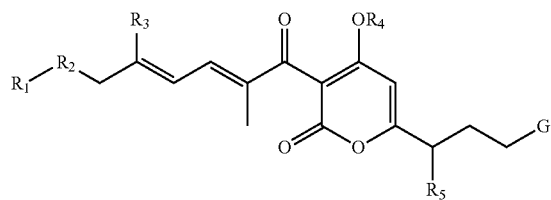

I or a salt thereof, wherein:
$R^1$ is one of $CF_3$, $CHF_2$, and $CH_2F$;
$R^2$ is absent or is $C_1$-$C_8$ alkyl, optionally substituted with halo;
$R^3$, $R^4$, and $R^5$ are independently H or methyl;
G is one of —CH=CH—NHC(O)—$R^6$, —CH=CH—NHC(S)—$R^6$, —$CH_2CH_2$NHC(O)—$R^6$, —$CH_2CH_2$NHC(S)—$R^6$, —$CH_2$NHNHC(O)—$R^6$, or —$CH_2$NHNHC(S)—$R^6$,
$R^6$ is one of $C_1$-$C_6$ alkyl, —O($C_1$-$C_6$ alkyl), —S($C_1$-$C_6$ alkyl), or —N(R)$_2$; and
each $R^7$ is independently H or —$C_1$-$C_6$ alkyl.

In certain embodiments, $R^2$ is $C_1$-$C_8$ alkyl, optionally substituted with halo.

$R^5$ may be H or methyl. When $R^5$ is methyl, it will be attached to chiral carbon. With respect to this chiral center, compounds of general structural formula (I) may exist as the R configuration, as the S configuration, or as a mixture of R and S stereoisomers.

One preferred embodiment relates to compounds of general structural formula (I) where $R^5$ is methyl and where the compound is a mixture of the R and S stereoisomers.

One preferred embodiment relates to compounds of general structural formula (I) where $R^5$ is methyl and where the compound is predominantly the R stereoisomer, preferably at least 90% of the R isomer.

Certain embodiments of the invention also provide methods for preparation of a compound according to general structural formula (I).

Certain embodiments of the invention also provide an assay for inhibition of a RNA polymerase comprising contacting a bacterial RNA polymerase with a compound according to general structural formula (I).

Certain embodiments of the invention also provide an assay for antibacterial activity comprising contacting a bacterial RNA polymerase with a compound according to general structural formula (I).

Certain embodiments of the invention also provide the use of a compound according to general structural formula (I) as an inhibitor of a bacterial RNA polymerase.

Certain embodiments of the invention also provide the use of a compound according to general structural formula (I) as an antibacterial agent.

Certain embodiments of the invention also provide the use of a compound according to general structural formula (I) as one of a disinfectant, a sterilant, an antispoilant, an antiseptic, and an antiinfective.

Compound Synthesis

Compounds of Formula I may be prepared by the synthetic Scheme 1 shown below, and by reference to analogous chemistry known in the art as well as synthetic examples presented herein. Useful literature references are those that describe the synthesis of other alpha-pyrone compounds. See Lira, R. et al., (2007) Bioorg. Med. Chem. Letters 17, 6797-6800; Doundoulakis, T. et al. (2004), Bioorg. Med. Chem. Letters 14, 5667-5672; Xiang, A. X. et al. (2006), Heterocycles 68, 1099-1103; Wardenga, G., (2007) Enwicklung eines synthetischen Zugangs zu potentiellen Antibiotika auf Basis der Naturstoffs Corallopyronin A. Thesis, (Gottfried Wilhelm Leibniz Universitat, Hannover, Germany); and U.S. Pat. Nos. 6,239,291; 6,191,288; and 6,022,983.

Scheme 1 General Scheme for Preparing Certain Compounds of Formula I

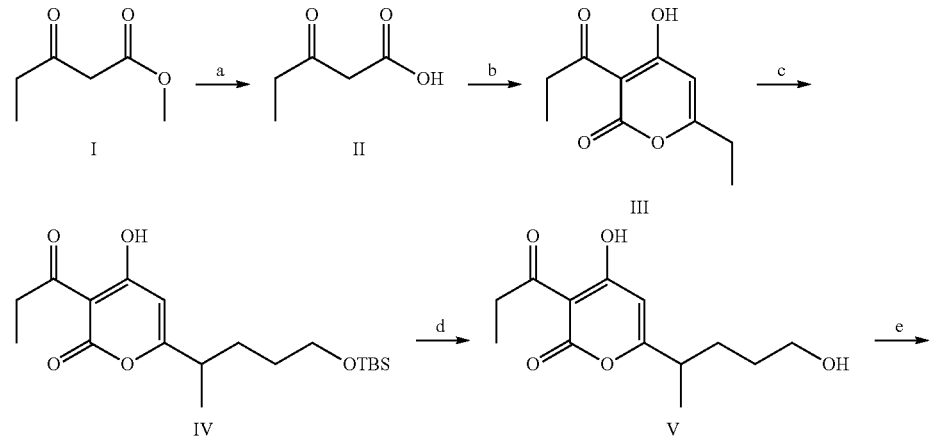

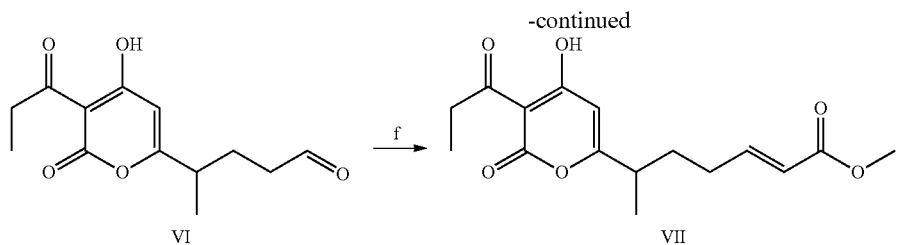
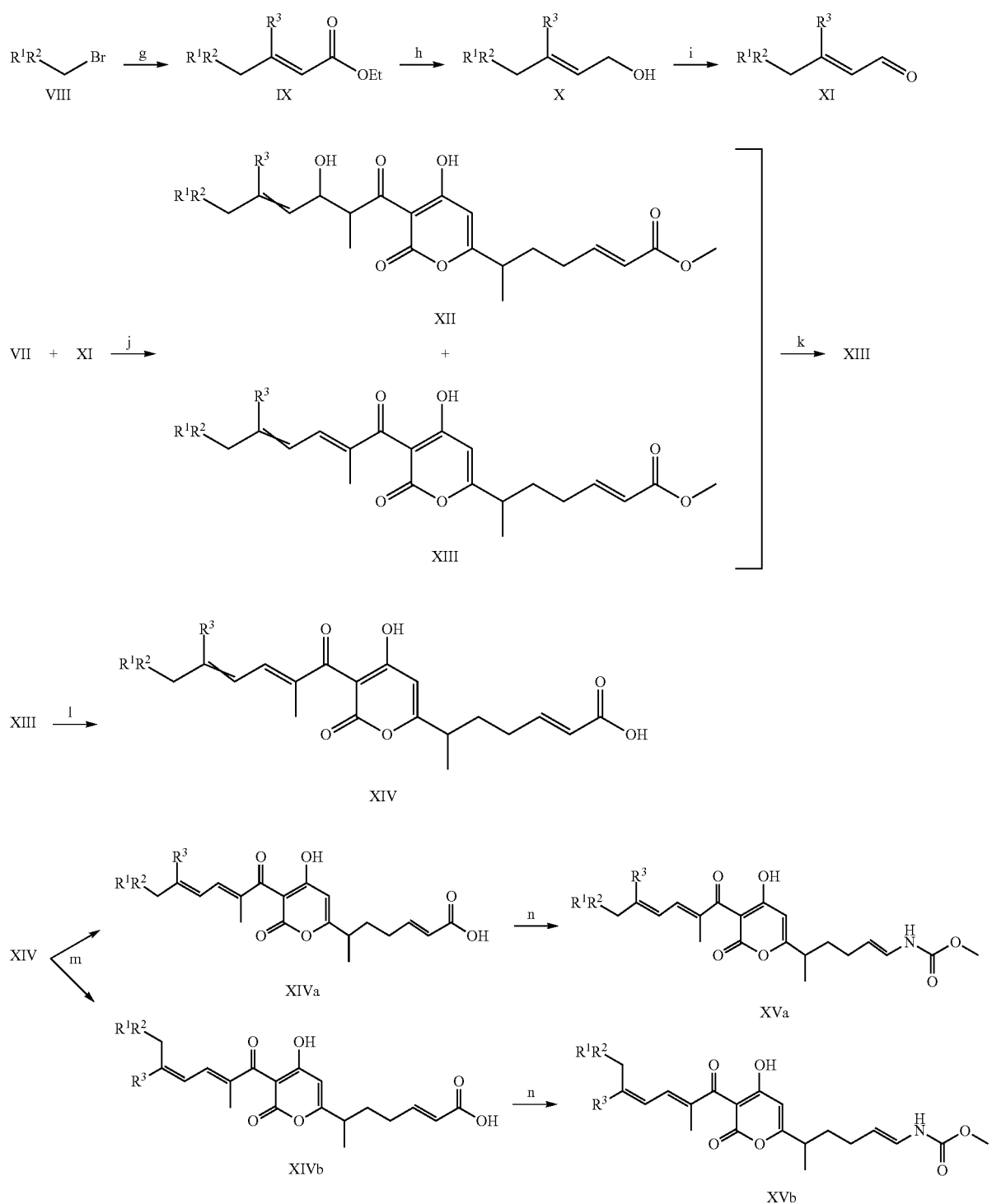

-continued

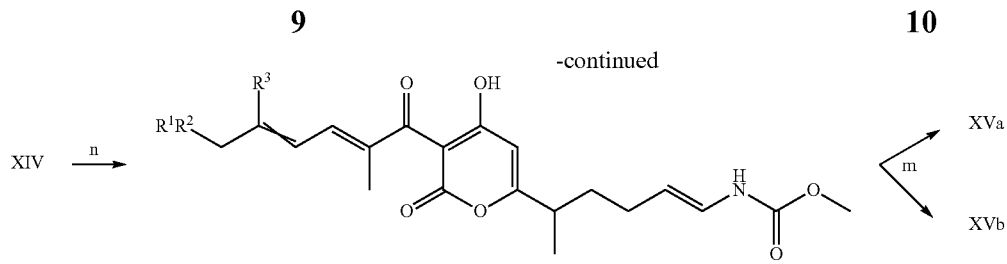

Reagents and conditions: a = NaOH; b = CDI; c = LDA, Br—Pr—OTBS;
d = AcOH, THF, H₂O; e = sodium periodinate, pyridine; f = NaH, trimethyl
phosphonoacetate; g = (1) Mg turnings, TEMED, (2) filtered into ethyl-2-butynoate; h = DIBAH;
i = TPAP/NMO; j = TiCl₄, DIPEA; k (optional reaction; performed only if yield of XII is significant) =
p-toluene sulfonic acid, benzene; I = LiOH; m = RP—HPLC; n = (1) EtOCOCl, DIPEA, NaN₃, (2)
toluene extraction, (3) toluene/MeOH reflux Scheme 1 above shows a general route for preparing certain compounds of formula I. The scheme is illustrated for compounds where $R^4$ is —H, $R^5$ is —CH₃, and G is —CH═CH—NHC(O)—CH₃. One skilled in the art will understand how the general scheme may be modified in various ways to obtain other compounds of Formula I. Furthermore, one skilled in the art will appreciate that compounds III-XIVb in Scheme 1 are useful intermediates for obtaining further compounds of Formula I by methods that are well-known in the art.

In Scheme 1 above, a crossed-double-bond symbol denotes an unspecified double-bond configuration (i.e., a mixture of E configuration and Z configuration).

Administration of Pharmaceutical Compositions

The compounds of Formula I may be formulated as pharmaceutical compositions and administered to a mammalian host, such as a human patient in a variety of forms adapted to the chosen route of administration (i.e., orally or parenterally, by intravenous, intramuscular, topical or subcutaneous routes).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, *acacia*, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 200 mg/kg, e.g., from about 1 to about 100 mg/kg of body weight per day, preferably in the range of 2 to 50 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following illustrate representative preferred pharmaceutical dosage forms, containing a compound of formula I, or a pharmaceutically acceptable salt thereof, ('Compound X'), for therapeutic or prophylactic use in humans:

a) A formulation comprising from about 0.0.1 mg/ml to about 10 mg/ml of Compound X, about 0% to about 10% dimethylacetamide, and about 0% to about 8% Cremophor EL, and having a pH of at least about 6;

b) A formulation comprising from about 0.6 mg/ml to about 6 mg/ml of Compound X, about 0% to about 7.5% dimethylacetamide, and about 0% to about 6% Cremophor EL, and having a pH of at least about 7;

c) A formulation comprising about 3 mg/ml of Compound X, about 5% dimethylacetamide, and about 4% Cremophor EL, and having a pH of about 7.4.

The invention will now be illustrated by the following non-limiting Examples.

EXAMPLES

Example Compounds

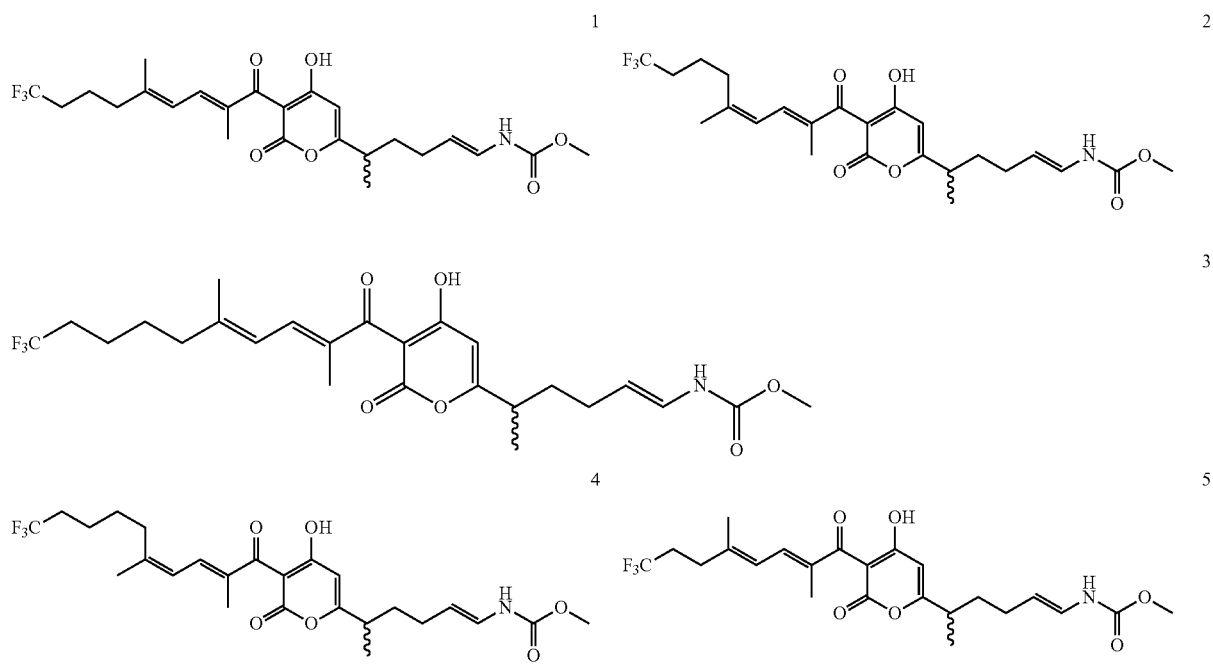

-continued
6
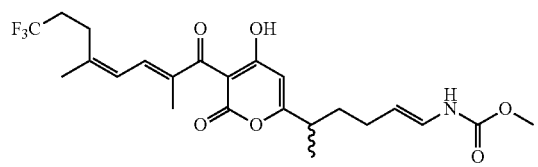
7
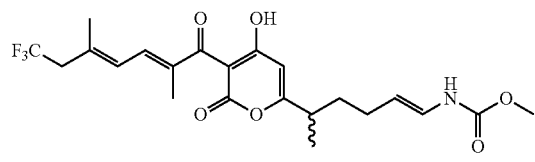
8
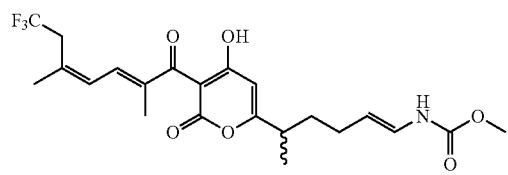
9
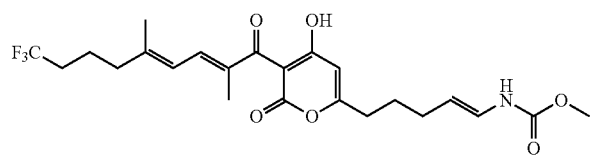
10
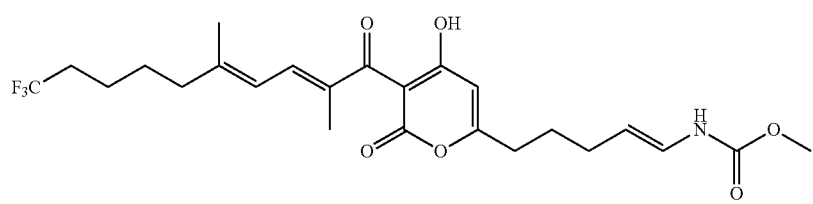
11
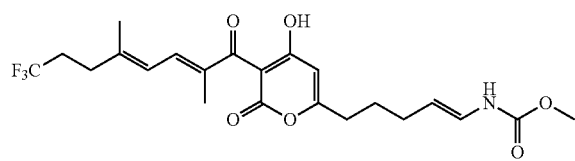
12
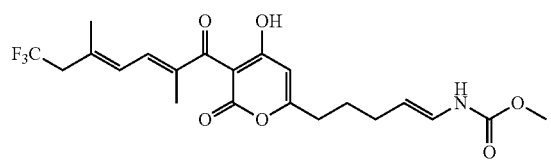
13
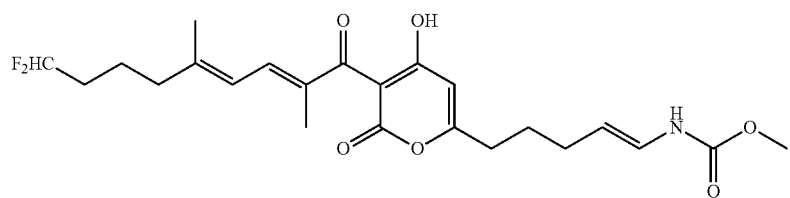
14
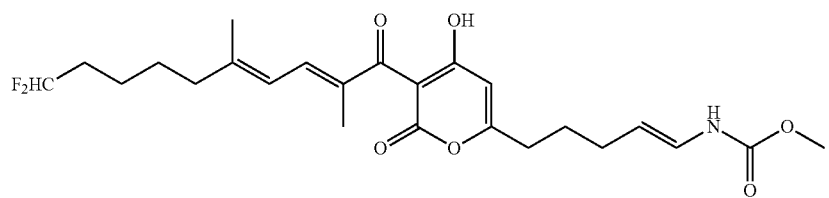
15
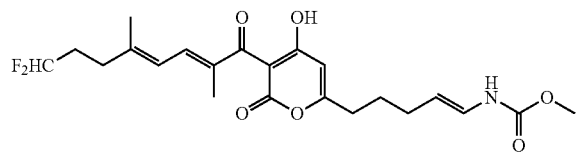
16
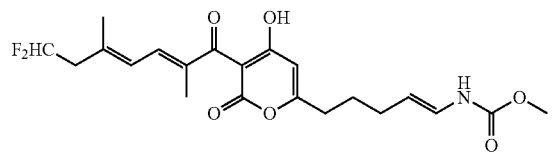

Example 1

Methyl ((E)-5-(4-hydroxy-2-oxo-3-((2E,4E)-9,9,9-trifluoro-2,5-dimethylnona-2,4-dienoyl)-2H-pyran-6-yl)hex-1-en-1-yl)carbamate (compound 1; XVa in Scheme 1, where $R^1$=—$CF_3$, $R^2$=—$CH_2CH_2$—, and $R^3$=—$CH_3$)

rated $NH_4Cl$, extracted with 3×20 ml EtOAc, dried with anhydrous $Na_2SO_4$, and evaporated to an oil. The product was purified via silica chromatography (10% EtOAc in hexanes).

Yield: 0.588 g, 62.5%.

$^1$H-NMR (400 MHz, $CDCl_3$): δ 0 (s, 6H), 0.82 (s, 9H), 1.18 (t, 3H), 1.22 (d, 3H), 1.60 (m, 2H) 1.75 (m, 2H), 2.58 (m, 1H), 3.05 (q; 2H), 3.58 (t, 2H), 5.86 (s, 1H).

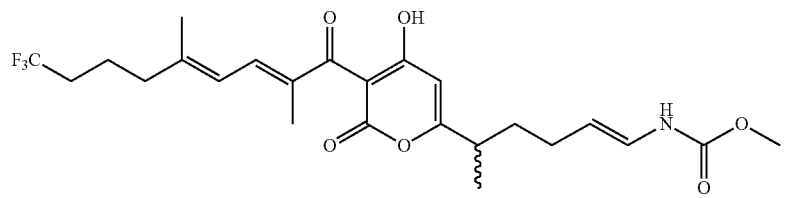

1

Example 1.1

3-Oxopentanoic acid (II in Scheme 1)

Methyl propionylacetate (I in Scheme 1; 10 g; 769 mmol; Aldrich) was stirred in 60 ml 1.5 M NaOH for 24 h at 25° C. The reaction mixture was diluted with 60 ml ice water, acidified with 3N HCl to pH 2, and solid KCl was added to saturation. The reaction mixture was extracted with 5×50 ml EtOAc, and the organic layers were pooled, dried with anhydrous $Na_2SO_4$, and evaporated to a white solid.

Yield: 8.9 g, 95%.

Example 1.24

6-Ethyl-4-hydroxy-3-propionyl-2-H-pyran-2-one (III in Scheme 1)

3-Oxopentanoic acid (II in Scheme 1; Example 1.1; 2 g; 17.2 mmol) was dissolved in 30 ml THF and cooled to 0° C. To the solution, was added dicarbodiimidazole (3.6 g; 22.2 mmol; Aldrich). The reaction mixture was stirred for 18 h at 25° C., neutralized with 2% HCl, extracted with 3×30 ml EtOAc, dried with anhydrous $Na_2SO_4$, and evaporated to a white solid. The product was purified via silica chromatography (20% EtOAc in hexanes).

Yield: 1.3 g, 77%.

$^1$H-NMR (400 MHz, $CDCl_3$): δ 1.09 (t, 3H), 1.11 (t, 3H), 2.46 (q, 2H), 3.05 (q, 2H), 5.86 (s; 1H).

Example 1.3

6-(5-(t-Butyldimethylsilyloxy)pentan-2-yl)-4-hydroxy-3-propionyl-2-H-pyran-2-one (IV in Scheme 1)

6-Ethyl-4-hydroxy-3-propionyl-2-H-pyran-2-one (III in Scheme 1; Example 1.2; 0.5 g; 2.56 mmol) was dissolved in 20 ml anhydrous THF and cooled to 0° C. under argon. To the cooled solution, was added LDA (5.12 ml of 1.5 M solution in cyclohexane; 7.68 mmol; Aldrich) and the reaction mixture was stirred for 30 min. To the cooled reaction mixture, was added 3-bromopropoxy-t-butyldimethylsilane (0.77 g; 3.07 mmol; Aldrich) and 1 ml HMPA (Aldrich). The reaction mixture was stirred for 30 min at 0° C., quenched with satu-

Example 1.4

4-(5-Hydroxy-2-oxo-3-propionyl-2-H-pyran-6-yl) pentanol (V in Scheme 1)

6-(5-(t-Butyldimethylsilyloxy)pentan-2-yl)-4-hydroxy-3-propionyl-2-H-pyran-2-one (IV in Scheme 1; Example 1.3; 3 g; 8.15 mmol) in 100 ml AcOH/THF/water (3/1/1, v/v/v) was stirred for 18 h at 25° C. The reaction mixture was neutralized with saturated $NaHCO_3$, extracted with 3×50 ml EtOAc, dried with anhydrous $Na_2SO_4$, and evaporated to an oil. The product was purified via silica chromatography (40% EtOAc in hexanes).

Yield: 1.05 g, 53%.

$^1$H-NMR (400 MHz, $CDCl_3$): δ 1.18 (t, 2H), 1.22 (d, 3H), 1.60 (m, 2H) 1.75 (m, 2H), 2.58 (m, 1H), 3.05 (q; 2H), 3.62 (t, 2H), 5.86 (s, 1H).

Example 1.5

4-(5-Hydroxy-2-oxo-3-propionyl-2-H-pyran-6-yl) pentanal (VI in Scheme 1)

4-(5-Hydroxy-2-oxo-3-propionyl-2-H-pyran-6-yl)pentanol (V in Scheme 1; Example 1.4; 0.38 g; 1.5 mmol; Aldrich) was dissolved in 20 ml dichloromethane and 0.6 ml pyridine. Sodium periodinate (0.7 g; 1.65 mmol; Aldrich) was added and stirred for 2 h at 25° C., after which reaction mixture was neutralized with saturated $NaHCO_3$ and extracted with 3×20 ml $CH_2Cl_2$. The pooled organic extracts were dried with anhydrous $Na_2SO_4$, evaporated, and purified via silica chromatography (20% EtOAc in hexanes).

Yield: 0.124 g, 33.3%.

$^1$H-NMR (400 MHz, $CDCl_3$): δ 1.18 (t, 3H), 1.26 (d, 3H), 1.90 (m, 1H), 2.05 (m, 1H), 2.50 (t, 2H), 2.62 (q, 1H), 3.10 (q, 2H), 5.95 (s; 1H), 9.80 (s, 1H).

Example 1.6

(E)-Methyl 6-(4-hydroxy-2-oxo-3-propionyl-2-H-pyran-6-yl)hept-2-enoate (VII in Scheme 1)

NaH (0.06 g; 1.5 mmol; 60% dispersion in mineral oil; Aldrich) was added to trimethyl phosphonoacetate (0.190 g; 1.0 mmol; Aldrich) in 10 ml THF. The reaction mixture was stirred at 25° C. for 15 min, after which 4-(4-hydroxy-2-oxo-3-propionyl-2H-pyran-6-yl)pentanal (VI in Scheme 1; Example 1.5; 0.124 g; 0.5 mmol) in 10 ml THF was added.

The reaction mixture was stirred at 25° C. for 4 h, quenched with saturated NH$_4$Cl, extracted with 3×20 ml EtOAc, dried with anhydrous Na$_2$SO$_4$, and evaporated. The product was purified via silica flash chromatography (40% EtOAc in hexanes).

Yield: 0.089 g, 58%.

$^1$H-NMR (400 MHz, CDCl$_3$): δ 1.15 (t, 3H), 1.28 (d, 3H), 1.70 (m, 1H), 1.90 (m, 1H), 2.22 (q, 2H), 2.60 (m, 1H), 3.07 (q, 2H), 3.73 (s, 3H), 5.85 (d, 1H), 5.95 (s, 1H), 6.90 (m, 1H).

Example 1.7

(E)-Ethyl 7,7,7-trifluoro-3-methylhept-2-enoate (IX in Scheme 1, where R$^1$=—CF$_3$, R$^2$=—CH$_2$CH$_2$—, and R$^3$=—CH$_3$)

To a suspension of magnesium turnings (0.8 g; 33 mmol; Aldrich) and a crystal of iodine in 20 ml anhydrous diethyl ether, trifluorobutyl bromide (VIII in Scheme 1, where R$^1$=—CF$_3$, R$^2$=—CH$_2$CH$_2$—, and R$^3$=—CH$_3$; 5.77 g; 30 mmol; SynQuest) in 20 ml diethyl ether was added dropwise over 2 h. The reaction was allowed to stir overnight under argon. Stirring was stopped, and solids were allowed to settle to the bottom of the reaction flask. The supernatant was transferred to a round-bottom flask containing copper iodide (4.42 g; 23.2 mmol; Aldrich), and TEMED (8.69 g, 75 mmol; Aldrich) in 40 ml anhydrous THF. The reaction mixture was stirred for 90 min at 25° C. and then brought to −72° C. Ethyl 2-butynoate (2.27 ml; 19 mmol; Aldrich) in 5 ml THF was added in three portions over 15 min, the suspension was stirred for an additional 90 min, and the reaction was quenched by addition of 10 ml MeOH, followed by 20 ml saturated NH$_4$Cl, with stirring. The ethanol/dryice bath was removed, and the suspension was allowed to reach room temperature. The suspension was filtered, and the solid was rinsed with ether. The filtrate was extracted 3x with ether, and the organic extracts were pooled, dried with anhydrous sodium sulfate, and evaporated to 3.3 g of yellowish oil.

Yield: 3.3 g, 49% crude.

$^1$H-NMR (500 MHz, CDCl$_3$): δ 1.28 (t, 3H), 1.78 (m, 2H), 2.05 (m, 2H), 2.16 (s, 3H), 2.22 (m, 2H), 4.15 (q, 2H), 5.57 (s, 1H).

Example 1.8

(E)-7,7,7-trifluoro-3-methyl-hept-2-enol (X in Scheme 1, where R$^1$=—CF$_3$, R$^2$=—CH$_2$CH$_2$—, and R$^3$=—CH$_3$)

(E)-Ethyl 7,7,7-trifluoro-3-methylhept-2-enoate (IX in Scheme 1, where R$^1$=—CF$_3$, R$^2$=—CH$_2$CH$_2$—, and R$^3$=—CH$_3$; Example 1.7; 3.3 g; 14.73 mmol) was dissolved in 30 ml anhydrous THF and brought to −72° C. 1 M DIBAH in hexanes (29.46 ml; 29 mmol; Aldrich) was added dropwise over 30 min under argon. The dry-ice bath was removed, and the reaction mixture was stirred for an additional 1 h at room temperature. 40 ml ether was added, and the reaction mixture was cooled to 0° C. 1.2 ml water, 1.2 ml 15% NaOH, and 0.32 ml water successively were added, the ice bath was removed, and the reaction mixture was stirred for 15 min at 25° C. The reaction mixture was dried with anhydrous MgSO$_4$ and stirred for an additional 15 min. The reaction mixture was filtered, and the filtrate was evaporated to 1.3 g of colorless oil. Yield: 1.3 g, 49%.

$^1$H-NMR (300 MHz, CDCl$_3$): δ 1.65 (s, 3H), 1.60-1.80 (m, 2H), 2.00-2.20 (m, 4H), 4.20 (d, 2H), 5.50 (t, 1H).

Example 1.9

(E)-7,7,7-trifluoro-3-methylhept-2-enal (XI in Scheme 1, where R$^1$=—CF$_3$, R$^2$=—CH$_2$CH$_2$—, and R$^3$=—CH$_3$)

(E)-7,7,7-trifluoro-3-methyl-2-heptenol (X in Scheme I, where R$^1$=—CF$_3$, R$^2$=—CH$_2$CH$_2$—, and R$^3$=—CH$_3$; Example 1.8; 1.3 g; 7.14 mmol) was dissolved in 20 ml CH$_2$Cl$_2$. To the solution, was added 4.3 g 4 Å molecular sieves (Aldrich), NMO (1.82 g; 15.48 mmol; Aldrich), and TPAP (0.163 g; 0.43 mmol; Aldrich). The suspension was stirred in the dark under argon for 30 min. The product was purified via silica chromatography (eluent: CH$_2$Cl$_2$).

Yield: 0.94 g, 73%.

$^1$H-NMR (400 MHz, CDCl$_3$): δ 1.75-1.85 (m, 2H), 2.05-2.15 (m, 2H), 2.18 (s, 3H), 2.30 (t, 2H), 5.89 (d; 1H), 9.99 (d, 1H).

Example 1.10

(E)-methyl 6-(4-hydroxy-2-oxo-3-((2E,4E/Z)-9,9,9-trifluoro-2,5-dimethylnona-2,4-dienoyl)-2H-pyran-6-yl)hept-2-enoate (XIII in Scheme 1, where R$^1$=—CF$_3$, R$^2$=—CH$_2$CH$_2$—, and R$^3$=—CH$_3$)

To (E)-Methyl 6-(4-hydroxy-2-oxo-3-propionyl-2-H-pyran-6-yl)hept-2-enoate (VII in Scheme 1; Example 1.6; 0.5 g; 1.62 mmol) in 30 ml anhydrous CH$_2$Cl$_2$ at −72° C., was added TiCl$_4$ (0.708 ml; 6.48 mmol; Aldrich) under argon. The reaction was stirred for 1 h, after which DIPEA (1.41 ml; 8.1 mmol; Aldrich) was added. After stirring at −72° C. for 2 h, (E)-7,7,7-trifluoro-3-methylhept-2-enal (XI in Scheme 1, where R$^1$=—CF$_3$, R$^2$=—CH$_2$CH$_2$—, and R$^3$=—CH$_3$; Example 1.9; 0.94 g; 5.21 mmol) in 5 ml anhydrous CH$_2$Cl$_2$ was added in two portions over 10 min. The reaction was stirred at −72° C. for 2 days, stirred at 0° C. for 1 h, quenched with 20 ml ice water, and extracted with 2×20 ml CH$_2$Cl$_2$. The pooled organic extracts were washed with saturated NH$_4$Cl, washed twice with saturated NaHCO$_3$, dried with anhydrous Na$_2$SO$_4$, and evaporated to a brown semi-solid.

Yield: 288 mg, 38%.

$^1$H-NMR (400 MHz, CDCl$_3$): δ 1.28 (d, 3H) 1.68-1.80 (overlapping m, 4H), 1.85 (s, 3H), 2.01 (s, 3H), 2.08 (m, 2H) 2.25 (overlapping m, 4H), 2.60 (m, 1H), 3.72 (s; 3H) 5.85 (d, 1H), 5.95 (s, 1H), 6.18 (d, 1H), 6.90 (d, 1H), 7.00 (m, 1H).

Example 1.11

(E)-6-(4-hydroxy-2-oxo-3-((2E,4E)-9,9,9-trifluoro-2,5-dimethylnona-2,4-dienoyl)-2H-pyran-6-yl)hept-2-enoic acid (XIVa in Scheme 1, where R$^1$=—CF$_3$, R$^2$=—CH$_2$CH$_2$—, and R$^3$=—CH$_3$)

To a solution of (E)-methyl 6-(4-hydroxy-2-oxo-3-((2E,4E/Z)-9,9,9-trifluoro-2,5-dimethylnona-2,4-dienoyl)-2H-pyran-6-yl)hept-2-enoate (XIII in Scheme 1, where R$^1$=—CF$_3$, R$^2$=—CH$_2$CH$_2$—, and R$^3$=—CH$_3$; Example 1.10; 288 mg; 0.61 mmol) in 33 ml THF, was added 8.36 ml 1 M LiOH (8.36 mmol; Aldrich). The reaction mixture was stirred for 35 h at 25° C. EtOAc (30 ml) was added, and the reaction mixture was acidified with 3 N HCl to pH 2 and extracted with 3×10 ml EtOAc. The organic extracts were pooled, evaporated, and purified via semi-preparative RPCl8-HPLC (Phenomenx Jupiter C18, 300 Å, 10 micron, 25 cm×10 mm column; mobile phase A, MeOH/H$_2$O/AcOH, 70/30/4, v/v/v; mobile phase B, MeOH/H$_2$O/AcOH, 90/10/4, v/v/v; gradient, 30 min 0% B, 50 min, 100% B; flow rate, 2 ml/min).

XIVa eluted at 20 min. XIVb eluted at 16 min.

XIVa: Yield: 32 mg, 12%.

$^1$H-NMR (400 MHz, CDCl$_3$): δ 1.28 (d, 3H) 1.68-1.80 (overlapping m, 4H), 1.85 (s, 3H), 2.01 (s, 3H), 2.08 (m, 2H) 2.25 (overlapping m, 4H), 2.60 (m, 1H), 5.85 (d, 1H), 5.95 (s, 1H), 6.18 (d, 1H), 6.90 (d, 1H), 7.00 (m, 1H).

XIVb: Yield: 21 mg, 8%.

$^1$H-NMR (400 MHz, CDCl$_3$): δ 1.28 (d, 3H) 1.68-1.80 (overlapping m, 4H), 1.94 (s, 3H), 2.01 (s, 3H), 2.08 (m, 2H) 2.25 (overlapping m, 4H), 2.60 (m, 1H), 5.85 (d, 1H), 5.95 (s, 1H), 6.18 (d, 1H), 6.90 (d, 1H), 7.00 (m, 1H).

Example 1.12

Methyl ((E)-5-(4-hydroxy-2-oxo-3-((2E,4E)-9,9,9-trifluoro-2,5-dimethylnona-2,4-dienoyl)-2H-pyran-6-yl)hex-1-en-1-yl)carbamate (compound 1; XVa in Scheme 1, where R$^1$=—CF$_3$, R$^2$=—CH$_2$CH$_2$—, and R$^3$=—CH$_3$)

(E)-6-(4-hydroxy-2-oxo-3-((2E,4E)-9,9,9-trifluoro-2,5-dimethylnona-2,4-dienoyl)-2H-pyran-6-yl)hept-2-enoic acid (XIVa in Scheme 1, where R$^1$=—CF$_3$, R$^2$=—CH$_2$CH$_2$—, and R$^3$=—CH$_3$; Example 1.11; 24 mg; 0.053 mmol) was dissolved in 8 ml acetone (distilled over P$_2$O$_5$) and cooled to 0° C. DIPEA (80 µl; 0.462 mmol; Aldrich) was added, followed by ethyl chloroformate (40 µl; 0.416 mmol; Aldrich). The reaction mixture was stirred for 90 min, after which NaN$_3$ (40 mg in 320 µl water, 0.70 mmol; Aldrich) was added and stirred for 70 min. Ice water (15 ml) was added, the reaction mixture was extracted with 3×20 ml toluene, and the pooled organic extracts were dried with anhydrous Na$_2$SO$_4$ and evaporated to an oil. The oil was left under high vacuum for 15 min, and then was dissolved in 8 ml anhydrous toluene, refluxed under argon for 2 h, cooled to 80° C., supplemented with 4 ml anhydrous MeOH, and maintained at 80° C. for 14 h. The sample was evaporated, and the product was purified via silica flash chromatography (EtOAc gradient in hexanes).

Yield: 11 mg, 43%.

$^1$H-NMR (500 MHz, CDCl$_3$): δ 1.24 (d, 3H), 1.26 (m, 2H), 1.60-1.80 (m, 4H), 1.85 (s, 3H), 2.01 (s, 3H), 2.08 (m, 2H), 2.08 (m, 2H), 2.60 (m, 1H), 3.71 (s, 3H), 4.95 (br m, 1H), 5.95 (s, 1H), 6.09 (d, 1H), 6.10 (br m, 1H), (6.46 (br t, 1H), 6.98 (d, 1H).

$^{19}$F-NMR (300 MHz, CDCl$_3$): δ −66.25 (s).

MS (MALDI): calculated: m/z 485.49 (MH$^+$). found: 486.52, 508.52.

Example 2

Methyl ((E)-5-(4-hydroxy-2-oxo-3-((2E,4Z)-9,9,9-trifluoro-2,5-dimethylnona-2,4-dienoyl)-2H-pyran-6-yl)hex-1-en-1-yl)carbamate (compound 2; XVb in Scheme 1, where R$^1$=—CF$_3$, R$^2$=—CH$_2$CH$_2$—, and R$^3$=—CH$_3$)

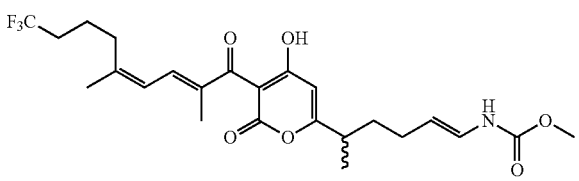

2

(E)-6-(4-hydroxy-2-oxo-3-((2E,4Z)-9,9,9-trifluoro-2,5-dimethylnona-2,4-dienoyl)-2H-pyran-6-yl)hept-2-enoic acid (XIVb in Scheme 1, where R$^1$=—CF$_3$, R$^2$=—CH$_2$CH$_2$—, and R$^3$=—CH$_3$; Example 1.11; 17 mg; 0.036 mmol) was dissolved in 6 ml acetone (distilled over P$_2$O$_5$) and cooled to 0° C. DIPEA (60 µl; 0.346 mmol; Aldrich) was added, followed by ethyl chloroformate (28 µl; 0.291 mmol; Aldrich). The reaction mixture was stirred for 90 min, after which NaN$_3$ (28 mg in 224 µl water, 0.59 mmol; Aldrich) was added and stirred for 70 min. Ice water (15 ml) was added, the reaction mixture was extracted with 3×20 ml toluene, and the pooled organic extracts were dried with anhydrous Na$_2$SO$_4$, and evaporated to an oil. The oil was left under high vacuum for 15 min, and then was dissolved in 6 ml anhydrous toluene, refluxed under argon for 2 h, cooled to 80° C., supplemented with 3 ml anhydrous MeOH, and maintained at 80° C. for 14 h. The sample was evaporated, and the product was purified via silica flash chromatography (EtOAc gradient in hexanes).

Yield: 6 mg, 34%.

$^1$H-NMR (500 MHz, CDCl$_3$): δ 1.24 (d, 3H), 1.26 (m, 2H), 1.60-1.80 (m, 4H), 1.91 (s, 3H), 2.01 (s, 3H), 2.08 (m, 2H), 2.25 (m, 2H), 2.60 (m, 1H), 3.71 (s, 3H), 4.95 (br m, 1H), 5.95 (s, 1H), 6.09 (d, 1H), 6.10 (br m, 1H), (6.46 (br t, 1H), 6.98 (d, 1H).

$^{19}$F-NMR (300 MHz, CDCl$_3$): δ −66.25 (s).

MS (MALDI): calculated: m/z 485.49 (MH$^+$). found: 486.52, 508.52.

Example 3

Methyl ((E)-5-(4-hydroxy-2-oxo-3-((2E,4E)-10,10,10-trifluoro-2,5-dimethyldeca-2,4-dienoyl)-2H-pyran-6-yl)hex-1-en-1-yl)carbamate (compound 3; XVa in Scheme 1, where R$^1$=—CF$_3$, R$^2$=—CH$_2$CH$_2$CH$_2$—, and R$^3$=—CH$_3$)

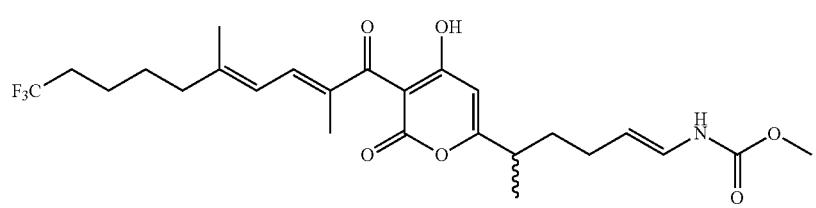

3

The compound was synthesized as for compound 1, except that trifluoropentyl bromide was used instead of trifluorobutyl bromide in the step corresponding to Example 1.7.

Yield: 9.4 mg, 24%.

$^1$H-NMR (500 MHz, CDCl$_3$): δ 1.24 (d, 3H), 1.26 (m, 4H), 1.60-1.80 (m, 4H), 1.85 (s, 3H), 2.01 (s, 3H), 2.08 (m, 2H), 2.25 (m, 2H), 2.60 (m, 1H), 3.71 (s, 3H), 4.95 (br m, 1H), 5.95 (s, 1H), 6.09 (d, 1H), 6.10 (br m, 1H), (6.46 (br t, 1H), 6.98 (d, 1H).

$^{19}$F-NMR (300 MHz, CDCl$_3$): δ −66.25 (s).

MS (MALDI): calculated: m/z 500.52 (MH$^+$). found: 500.21, 522.20.

Example 4

Methyl ((E)-5-(4-hydroxy-2-oxo-3-((2E,4E)-10,10,10-trifluoro-2,5-dimethyldeca-2,4-dienoyl)-2H-pyran-6-yl)hex-1-en-1-yl)carbamate (compound 4; XVb in Scheme 1, where R$^1$=—CF$_3$, R$^2$=—CH$_2$CH$_2$CH$_2$—, and R$^3$=—CH$_3$)

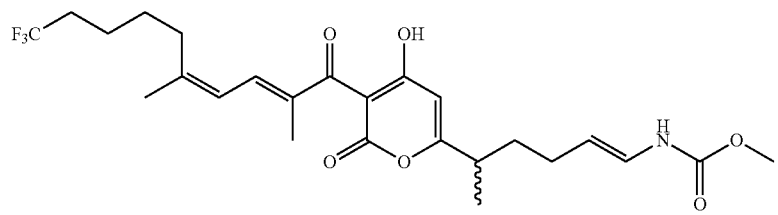

4

The compound is synthesized as for compound 2, except that trifluoropentyl bromide is used instead of trifluorobutyl bromide in the step corresponding to Example 1.7.

Example 5

Methyl ((E)-5-(4-hydroxy-2-oxo-3-((2E,4E)-10,10,10-trifluoro-2,5-dimethylocta-2,4-dienoyl)-2H-pyran-6-yl)hex-1-en-1-yl)carbamate (compound 5; XVa in Scheme 1, where R$^1$=—CF$_3$, R$^2$=—CH$_2$—, and R$^3$=—CH$_3$)

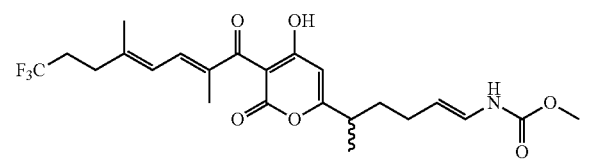

5

The compound was synthesized as for compound 1, except that trifluoropropyl bromide was used instead of trifluorobutyl bromide in the step corresponding to Example 1.7.

Yield: 72.4 mg, 43%.

$^1$H-NMR (500 MHz, CDCl$_3$): δ 1.24 (d, 3H), 1.60 (m, 2H), 1.80 (m, 2H), 1.87 (s, 3H), 2.02 (s, 3H), 2.35 (m, 2H), 2.45 (m, 2H), 2.60 (m, 1H), 3.71 (s, 3H), 4.95 (br m, 1H), 5.95 (s, 1H), 6.09 (d, 1H), 6.10 (br m, 1H), (6.46 (br t, 1H), 6.98 (d, 1H).

$^{19}$F-NMR (300 MHz, CDCl$_3$): δ −66.25 (s).

MS (MALDI): calculated: m/z 472.47 (MH$^+$). found: 472.22.52, 494.22.

Example 6

Methyl ((E)-5-(4-hydroxy-2-oxo-3-((2E,4Z)-10,10,10-trifluoro-2,5-dimethylocta-2,4-dienoyl)-2H-pyran-6-yl)hex-1-en-1-yl)carbamate (compound 6; XVb in Scheme 1, where R$^1$=—CF$_3$, R$^2$=—CH$_2$—, and R$^3$=—CH$_3$)

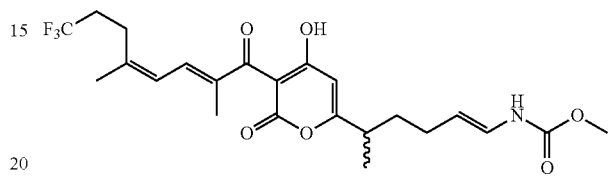

6

The compound is synthesized as for compound 2, except that trifluoropropyl bromide is used instead of trifluorobutyl bromide in the step corresponding to Example 1.7.

Example 7

Methyl ((E)-5-(4-hydroxy-2-oxo-3-((2E,4E)-7,7,7-trifluoro-2,5-dimethylhepta-2,4-dienoyl)-2H-pyran-6-yl)hex-1-en-1-yl)carbamate (compound 7; XVa in Scheme 1, where R$^1$=—CF$_3$, R$^2$ is absent, and R$^3$=—CH$_3$)

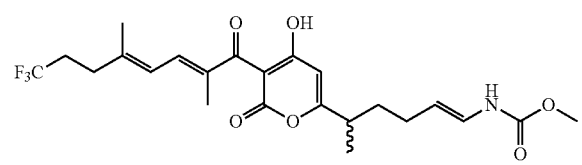

7

The compound is synthesized as for compound 1, except that trifluoroethyl bromide is used instead of trifluorobutyl bromide in the step corresponding to Example 1.7.

Example 8

Methyl ((E)-5-(4-hydroxy-2-oxo-3-((2E,4E)-7,7,7-trifluoro-2,5-dimethylhepta-2,4-dienoyl)-2H-pyran-6-yl)hex-1-en-1-yl)carbamate (compound 8; XVb in Scheme 1, where $R^1$=—$CF_3$, $R^2$ is absent, and $R^3$=—$CH_3$)

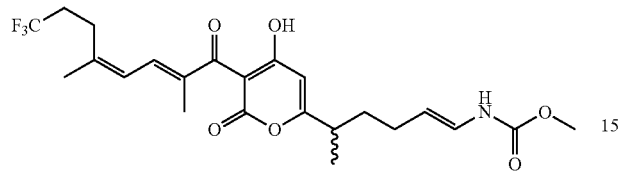

8

The compound is synthesized as for compound 2, except that trifluoroethyl bromide is used instead of trifluoroethyl bromide in the step corresponding to Example 1.7.

Example 9

Methyl ((E)-5-(4-hydroxy-2-oxo-3-((2E,4E)-9,9,9-trifluoro-2,5-dimethylnona-2,4-dienoyl)-2H-pyran-6-yl)pent-1-en-1-yl)carbamate (compound 9; $R^1$=—$CF_3$, $R^2$=—$CH_2CH_2$—, and $R^3$=—$CH_3$)

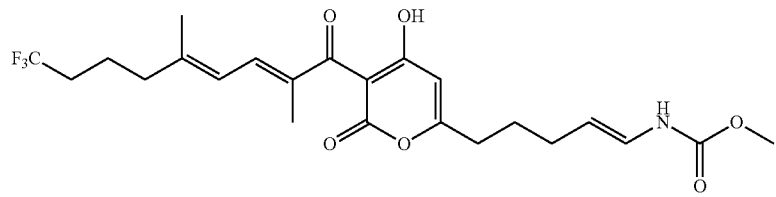

9

The compound was synthesized as for compound 1, except that 6-methyl-4-hydroxy-3-propionyl-2-H-pyran-2-one was used instead of III in the step corresponding to Example 1.3.
Yield: 5.6 mg, 8.2%.
$^1$H-NMR (500 MHz, CDCl$_3$): δ 1.26 (m, 2H), 1.60-1.80 (m, 4H), 1.85 (s, 3H), 2.01 (s, 3H), 2.08 (m, 2H), 2.25 (m, 2H), 2.60 (m, 2H), 3.71 (s, 3H), 4.95 (br m, 1H), 5.95 (s, 1H), 6.09 (d, 1H), 6.10 (br m, 1H), (6.46 (br t, 1H), 6.98 (d, 1H).
$^{19}$F-NMR (300 MHz, CDCl$_3$): δ −66.25 (s)
MS (MALDI): calculated: m/z 472.47 (MO. found: 472.02, 494.20.

Example 10

Methyl ((E)-5-(4-hydroxy-2-oxo-3-((2E,4E)-10,10,10-trifluoro-2,5-dimethyldeca-2,4-dienoyl)-2H-pyran-6-yl)pent-1-en-1-yl)carbamate (compound 10; $R^1$=—$CF_3$, $R^2$=—$CH_2CH_2CH_2$—, and $R^3$=—$CH_3$)

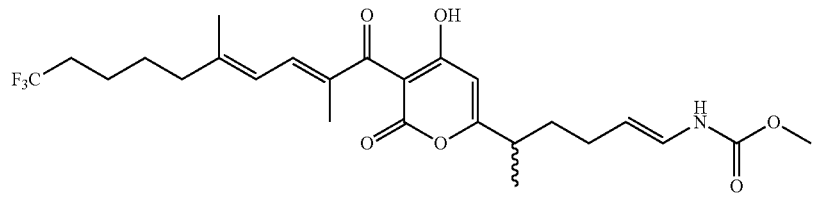

10

The compound is synthesized as for compound 1, except that 6-methyl-4-hydroxy-3-propionyl-2-H-pyran-2-one is used instead of III in the step corresponding to Example 1.3 and trifluoropentyl bromide is used instead of trifluorobutyl bromide in the step corresponding to Example 1.7.

Example 11

Methyl ((E)-5-(4-hydroxy-2-oxo-3-((2E,4E)-8,8,8-trifluoro-2,5-dimethylocta-2,4-dienoyl)-2H-pyran-6-yl)pent-1-en-1-yl)carbamate (compound 11; $R^1$=—$CF_3$, $R^2$=—$CH_2$—, and $R^3$=—$CH_3$)

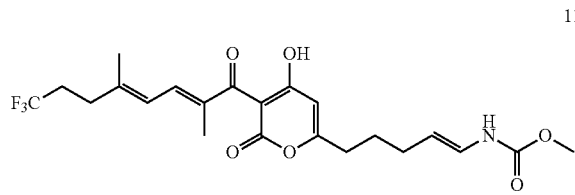 [SMILES: COC(=O)N/C=C/CCCc1cc(O)c(C(=O)/C(C)=C/C=C(\C)CCC(F)(F)F)c(=O)o1]

11

The compound was synthesized as for compound 1, except that 6-methyl-4-hydroxy-3-propionyl-2-H-pyran-2-one was used instead of III in the step corresponding to Example 1.3 and trifluoropropyl bromide was used instead of trifluorobutyl bromide in the step corresponding to Example 1.7.

Yield: 72.4 mg, 43%.

$^1$H-NMR (500 MHz, CDCl$_3$): δ 1.60 (m, 2H), 1.80 (m, 2H), 1.87 (s, 3H), 2.02 (s, 2.35 (m, 2H), 2.45 (m, 2H), 2.60 (m, 2H), 3.71 (s, 3H), 4.95 (br m, 1H), 5.95 (s, 1H), 6.09 (d, 1H), 6.10 (br m, 1H), (6.46 (br t, 1H), 6.98 (d, 1H).

$^{19}$F-NMR (300 MHz, CDCl$_3$): δ −66.25 (s).

MS (MALDI): calculated: m/z 458.44 (MH$^+$). found: 458.11, 480.10.

Example 12

Methyl RE)-5-(4-hydroxy-2-oxo-3-((2E,4E)-7,7,7-trifluoro-2,5-dimethylhepta-2,4-dienoyl)-2H-pyran-6-yl)pent-1-en-1-yl)carbamate (compound 12; $R^1$=—$CF_3$, $R^2$ is absent, and $R^3$=—$CH_3$)

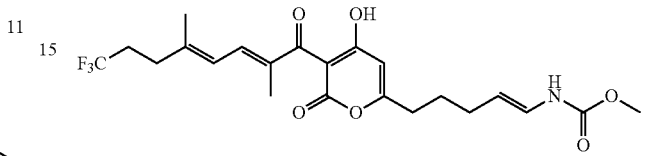

12

The compound is synthesized as for compound 1, except that 6-methyl-4-hydroxy-3-propionyl-2-H-pyran-2-one is used instead of III in the step corresponding to Example 1.3 and trifluoroethyl bromide is used instead of trifluorobutyl bromide in the step corresponding to Example 1.7.

Example 13

Methyl ((E)-5-(4-hydroxy-2-oxo-3-((2E,4E)-9,9-difluoro-2,5-dimethylnona-2,4-dienoyl)-2H-pyran-6-yl)pent-1-en-1-yl)carbamate (compound 13; $R^1$=—$CHF_2$, $R^2$=—$CH_2CH_2$—, and $R^3$=—$CH_3$)

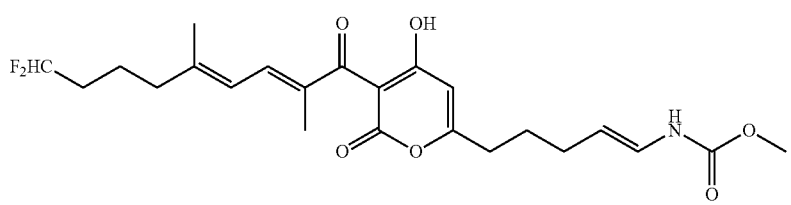

13

The compound is synthesized as for compound 1, except that 6-methyl-4-hydroxy-3-propionyl-2-H-pyran-2-one is used instead of III in the step corresponding to Example 1.3 and difluorobutyl bromide is used instead of trifluorobutyl bromide in the step corresponding to Example 1.7.

Example 14

Methyl ((E)-5-(4-hydroxy-2-oxo-3-((2E,4E)-10,10-difluoro-2,5-dimethyldeca-2,4-dienoyl)-2H-pyran-6-yl)pent-1-en-1-yl)carbamate (compound 14; $R^1$=—$CHF_2$, $R^2$=—$CH_2CH_2CH_2$—, and $R^3$=—$CH_3$)

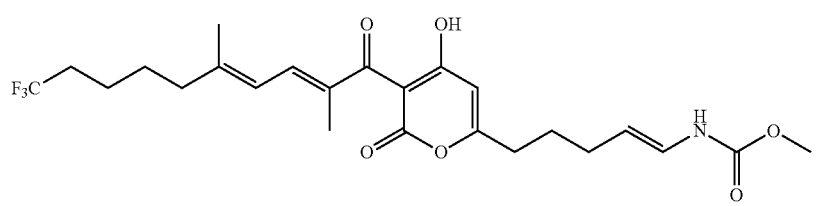

14

The compound is synthesized as for compound 1, except that 6-methyl-4-hydroxy-3-propionyl-2-H-pyran-2-one is used instead of III in the step corresponding to Example 1.3 and difluoropentyl bromide is used instead of trifluorobutyl bromide in the step corresponding to Example 1.7.

Example 15

Methyl ((E)-5-(4-hydroxy-2-oxo-3-((2E,4E)-8,8-difluoro-2,5-dimethylocta-2,4-dienoyl)-2H-pyran-6-yl)pent-1-en-1-yl)carbamate (compound 15; $R^1$=—CHF$_2$, $R^2$=—CH$_2$—, and $R^3$=—CH$_3$)

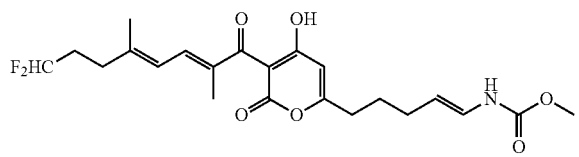

The compound is synthesized as for compound 1, except that 6-methyl-4-hydroxy-3-propionyl-2-H-pyran-2-one is used instead of III in the step corresponding to Example 1.3 and difluoropropyl bromide is used instead of trifluorobutyl bromide in the step corresponding to Example 1.7.

Example 16

Methyl ((E)-5-(4-hydroxy-2-oxo-3-((2E,4E)-7,7-difluoro-2,5-dimethylhepta-2,4-dienoyl)-2H-pyran-6-yl)pent-1-en-1-yl)carbamate (compound 16; $R^1$=—CHF$_2$, $R^2$ is absent, and $R^3$=—CH$_3$)

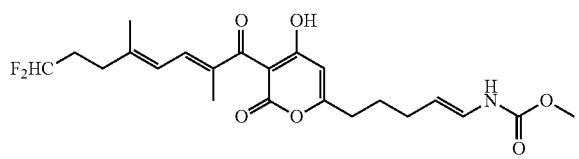

The compound is synthesized as for compound 1, except that 6-methyl-4-hydroxy-3-propionyl-2-H-pyran-2-one is used instead of III in the step corresponding to Example 1.3 and difluoroethyl bromide is used instead of trifluorobutyl bromide in the step corresponding to Example 1.7.

Example 17

Assay of Inhibition of Bacterial RNA Polymerase

Example 17.1

Assay of Inhibition of *Escherichia coli* RNA Polymerase

Fluorescence-detected RNA polymerase assays with *E. coli* RNA polymerase were performed by a modification of the procedure of Kuhlman et al., 2004 [Kuhlman, P., Duff, H. & Galant, A. (2004) A fluorescence-based assay for multi-subunit DNA-dependent RNA polymerases. *Anal. Biochem.* 324, 183-190]. Reaction mixtures contained (20 µl): 0-100 nM test compound, 75 nM *E. coli* RNA polymerase σ$^{70}$ holoenzyme, 20 nM 384 bp DNA fragment containing the bacteriophage T4 N25 promoter, 100 µM ATP, 100 µM GTP, 100 µM UTP, 100 µM CTP, 50 mM Tris-HCl, pH 8.0, 100 mM KCl, 10 mM MgCl$_2$, 1 mM DTT, 10 µg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 µl 5 mM CaCl$_2$ and 2 U DNaseI (Ambion, Inc.), followed by incubation for 90 min at 37° C. RNA was quantified by addition of 100 µl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)]. IC50 is defined as the concentration of inhibitor resulting in 50% inhibition of RNA polymerase activity.

Example 17.2

Assay of Inhibition of *Mycobacterium tuberculosis* RNA polymerase

Fluorescence-detected RNA polymerase assays with *M. tuberculosis* RNA polymerase were performed as in Example 17.1, using reaction mixtures containing (20 µl): 0-100 nM test compound, 75 nM *M. tuberculosis* RNA polymerase core enzyme, 300 nM *M. tuberculosis* σ$^A$, 20 nM 384 bp DNA fragment containing the bacteriophage T4 N25 promoter, 100 µM ATP, 100 GTP, 100 µM UTP, 100 µM CTP, 40 mM Tris-HCl, pH 8.0, 80 mM NaCl, 5 mM MgCl$_2$, 2.5 mM DTT, and 12.7% glycerol. IC50 is defined as the concentration of inhibitor resulting in 50% inhibition of RNA polymerase activity.

Example 17.3

Assay of Inhibition of *Staphylococcus aureus* RNA Polymerase

Fluorescence-detected RNA polymerase assays with *S. aureus* RNA polymerase were performed as in Example 17.1, using reaction mixtures containing (20 µl): 0-100 nM test compound, 75 nM *S. aureus* RNA polymerase core enzyme, 300 nM *S. aureus* σ$^A$, 20 nM 384 bp DNA fragment containing the bacteriophage T4 N25 promoter, 100 µM ATP, 100 µM GTP, 100 µM UTP, 100 µM CTP, 40 mM Tris-HCl, pH 8.0, 80 mM NaCl, 5 mM MgCl$_2$, 2.5 mM DTT, and 12.7% glycerol. IC50 is defined as the concentration of inhibitor resulting in 50% inhibition of RNA polymerase activity.

Example 18

Assay of Inhibition of Bacterial Growth in Culture

Example 18.1

Assay of Inhibition of Growth of *Staphylococcus aureus, Enterococcus faecalis*, and *Escherichia coli*

Minimum inhibitory concentrations (MICs) for methicillin-sensitive *Staphylococcus aureus* (MSSA) strain ATCC 12600, methicillin-resistant *Staphylococcus aureus* (MRSA)

strain BAA-1707 (USA-400; MW2), rifampin-resistant *Staphylococcus aureus* (RRSA) strain ATCC 12600-Rif (H526N), vancomycin-resistant *Staphylococcus aureus* (VRSA) strain VRS1, *Enterococcus faecalis* ATCC 19433, and *Escherichia coli* strain D21f2tolC were quantified using spiral gradient endpoint assays, essentially as described [Wallace, A. and Corkill, J. (1989) Application of the spiral plating method to study antimicrobial action. *J Microbiol. Meths.* 10, 303-310; Paton, J., Holt, A., and Bywater, M. (1990) Measurement of MICs of antibacterial agents by spiral gradient endpoint compared with conventional dilution methods. *Int. J. Exp. Clin. Chemother.* 3, 31-38; Schalkowsky S. (1994) Measures of susceptibility from a spiral gradient of drug concentrations. *Adv. Exp. Med. Biol.* 349, 107-120]. Assays employed exponential-gradient plates containing 150 mm×4 mm Mueller-Hinton II cation-adjusted agar and 0.4-100 µg/ml of test compound. Plates were prepared using an Autoplate 4000 spiral plater (Spiral Biotech, Inc.). Saturated overnight cultures were swabbed radially onto plates, and plates were incubated for 16 h at 37° C. For each culture, the streak length was measured using a clear plastic template (Spiral Biotech, Inc.), the test-compound concentration at the streak endpoint was calculated using the program SGE (Spiral Biotech, Inc.), and the MIC was defined as the calculated test-compound concentration at the streak endpoint.

Example 18.2

Assay of Inhibition of Growth of *Mycobacterium tuberculosis*

MICs for *Mycobacterium tuberculosis* strain H37Rv were quantified using microplate Alamar Blue assays as described [Collins, L. & Franzblau, S. (1997) Microplate Alamar Blue assay versus BACTEC 460 system for high-throughput screening of compounds against *Mycobacterium tuberculosis* and *Mycobacterium avium*. *Antimicrob. Agents Chemother.* 41, 1004-1009].

Example 18.3

Assay of Inhibition of Growth of *Bacillus anthracis*, *Francisella tularensis*, *Burkholderia mallei*, *Burkholderia pseudomallei*, and *Brucella melitensis*

MICs for *Bacillus anthracis* strain Vollum 1 b, *Francisella tularensis* strain SCHU4, *Burkholderia mallei* strain CHN7, *Burkholderia pseudomallei* strain Human/Blood/OH/US/1994, and *Brucella melitensis* strain 16M were quantified using broth microdilution assays as described [Clinical and Laboratory Standards Institute (CLSI/NCCLS) (2009) *Methods for Dilution Antimicrobial Susceptibility Tests for Bacteria That Grow Aerobically; Approved Standard, Eighth Edition. CLIS Document M07-A8* (CLIS, Wayne Pa.)].

Example 19

Assay of Antibacterial Efficacy in Mouse Model of *Staphylococcus Aureus* Systemic Infection ("Peritonitis Model")

Female Swiss Webster mice were experimentally infected by intraperitoneal administration of $1 \times 10^7$ colony forming units of methicillin-sensitive *Staphylococcus aureus* (MSSA) strain 8325-4 or $3 \times 10^6$ colony forming units of methicillin-resistant *Staphylococcus aureus* (MRSA) strain BAA-1707 (USA-400, MW2) in 5% hog gastric mucin. Test compounds (1.56, 3.13, and 6.25 mg/ml in vehicle [5% dimethylacetamide and 4% Cremophor EL in 100 mM sodium phosphate, pH 7.4]), positive control (1.56 mg/ml linezolid in vehicle), and negative control (vehicle only), were administered by intravenous injection into a tail vein (200 µl per injection) 0 h post-infection or oral gavage (400 µl per gavage) 1 h pre-infection. Survival was monitored for 24 h post-infection. Identities of test compounds and controls were blinded from personnel performing injections and monitoring survival. The protective dose 100 (PD 100) was defined as the test-compound dose resulting in 100% survival at 24 h. The protective dose 50 (PD50) was defined as the test-compound dose resulting in 50% survival at 24 h (calculated using the probit method).

Screening data for Example compounds of this invention and for the prior-art compound (±)myxopyronin B (Myx B) are presented in the following Tables.

TABLE 1

| | Inhibition of bacterial RNAP | | |
|---|---|---|---|
| compound | IC50 E. coli RNAP (nM) | IC50 M. tuberculosis RNAP (nM) | IC50 S. aureus RNAP (nM) |
| Myx B | 10 | 100 | 70 |
| 1 | 4 | 30 | 10 |
| 3 | 10 | 200 | 40 |
| 5 | 4 | 100 | 100 |
| 9 | 5 | 60 | |
| 11 | 20 | | |

TABLE 2

| | Inhibition of bacterial growth | | | | | |
|---|---|---|---|---|---|---|
| compound | MIC S. aureus MSSA 12600 (µg/ml) | MIC S. aureus MRSA BAA-1707 (µg/ml) | MIC S. aureus RRSA 12600-Rif (µg/ml) | MIC S. aureus VRSA VRS1 (µg/ml) | MIC E. faecalis 19433 (µg/ml) | MIC E. coli D21f2tolC (µg/ml) |
| Myx B | 0.6 | 0.9 | 1 | 0.5 | 20 | 0.1 |
| 1 | 0.3 | 0.5 | 1 | | 9 | 0.07 |
| 3 | 1 | 3 | 5 | | 10 | 0.3 |
| 5 | 0.9 | 1 | 2 | 0.5 | >40 | 0.2 |
| 9 | 0.9 | 0.8 | 1 | | 10 | 0.2 |
| 11 | 2 | 2 | 3 | 1 | >40 | 0.2 |

TABLE 3

Inhibition of bacterial growth

| compound | MIC B. anthracis Vollum1b (μg/ml) | MIC F. tularensis SCHU4 (μg/ml) | MIC B. mallei CHN7 (μg/ml) | MIC B. pseudomallei Human/Blood/ OH/US/1994 (μg/mL) | MIC B. melitensis 16M (μg/ml) |
|---|---|---|---|---|---|
| Myx B | 6 | 2 | 6 | 30 | 3 |
| 1 | 6 | 3 | 10 | 50 | 6 |

TABLE 4 clogD (calculated lipophilicity; calculated using ACD Percepta) and logD (experimental lipophilicity; determined using water:octanol partition with LC-MS detection) at pH 7.4

| compound | clogD (pH 7.4) | logD (pH 7.4) |
|---|---|---|
| Myx B | 2.4 | 1.8 |
| 1 | 2.2 | 1.4 |
| 2 | 2.2 | |
| 3 | 2.5 | |
| 4 | 2.5 | |
| 5 | 1.9 | |
| 6 | 1.9 | |
| 7 | 1.6 | |
| 8 | 1.6 | |
| 9 | 1.9 | |
| 10 | 2.2 | |
| 11 | 1.6 | |
| 12 | 1.3 | |
| 13 | 1.5 | |
| 14 | 1.8 | |
| 15 | 1.2 | |
| 16 | 0.9 | |

TABLE 5 serum shifts (MIC in presence of 10% of mouse serum divided by MIC n absence of 10% mouse serum; assayed using Escherichia coli D212f2tolC)

| compound | serum shift |
|---|---|
| Myx B | 16 |
| 1 | 8 |
| 3 | 16 |
| 5 | 8 |
| 9 | 8 |
| 11 | 4 |

TABLE 6 metabolic stability (stability in the presence of human liver microsomes)

| compound | half-life human liver microsomes (min) |
|---|---|
| Myx B | 3 |
| 1 | 14 |

TABLE 7

Antibacterial efficacy in mice: methicillin-sensitive Staphylococcus aureus (MSSA) peritonitis: intravenous administration of test compounds

| compound | PD100 (mg/kg) | PD50 (mg/kg) |
|---|---|---|
| Myx B | >50 | 30 |
| 1 | >25 | 20 |
| 5 | 25 | 7 |
| 9 | 25 | 10 |

TABLE 8

Antibacterial efficacy in mice: methicillin-resistant Staphylococcus aureus (MRSA) peritonitis: intravenous administration of test compounds

| compound | PD100 (mg/kg) | PD50 (mg/kg) |
|---|---|---|
| Myx B | 50 | 20 |
| 1 | 50 | 10 |

TABLE 9

Antibacterial efficacy in mice: methicillin-resistant Staphylococcus aureus (MRSA) peritonitis: oral administration of test compounds

| compound | PD100 (mg/kg) | PD50 (mg/kg) |
|---|---|---|
| Myx B | 100 | 40 |
| 5 | 50 | 20 |

The data in Table 1 indicate that certain compounds of this invention potently inhibit bacterial RNA polymerases.

The data in Table 1 further indicate that certain compounds of this invention are at least approximately 2 times more potent than prior-art compound (±)myxopyronin B in inhibiting a bacterial RNA polymerase.

The data in Tables 2-3 indicate that certain compounds of this invention potently inhibit the Gram-positive bacterial pathogens Staphylococcus aureus (including both drug-sensitive and drug-resistant strains), Enterococcus faecalis, and Bacillus anthracis, and the Gram-negative pathogens Francisella tularensis, Burkholderia mallei, Burkholderia pseudomallei, and Brucella melitensis.

The data in Table 2 further indicate that certain compounds of this invention are at least approximately 2 times more potent than prior-art compound (±)myxopyronin B in inhibiting the Gram-positive bacterial pathogens Staphylococcus aureus and Enterococcus faecalis.

The data in Table 4 indicate that certain compounds of this invention exhibit at least approximately 0.2 units lower clog D and/or log D at pH 7.4 (at least approximately 2 times lower lipophilicity at pH 7.4) than prior-art compound (±)myxopyronin B.

The data in Table 5 indicate that certain compounds of this invention exhibit at least approximately 2 times lower serum shifts (at least approximately 2 times lower serum protein binding) than prior-art compound (±)myxopyronin B.

The data in Table 6 indicate that compound 1 of this invention exhibits approximately 4 to 5 times higher metabolic stability (higher stability in the presence of human liver microsomes) than prior-art compound (±)myxopyronin B.

The data in Tables 7-9 indicate that certain compounds of this invention clear infection and prevent death in a mammal. Table 7 presents data from experiments with mice systemically infected with methicillin-sensitive *Staphylococcus aureus* (MSSA) and compounds administered intravenously. Table 8 presents data from experiments with mice systemically infected with methicillin-resistant *Staphylococcus aureus* (MRSA) and compounds administered intravenously. Table 9 presents data from experiments with mice systemically infected with methicillin-resistant *Staphylococcus aureus* (MRSA) and test compounds administered orally.

The data in Tables 7-9 further indicate that certain compounds of this invention are at least approximately 2 times more potent than prior-art compound (±)myxopyronin B in clearing infection and preventing death in a mammal.

The data in Tables 7-9 further indicate that certain compounds of this invention are able to clear infection and prevent death in a mammal upon when administered intravenously or when administered orally.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

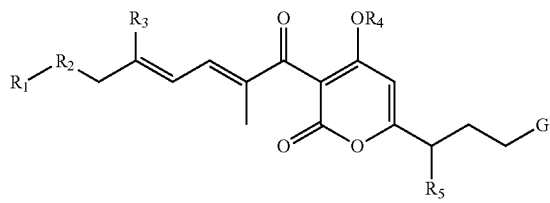

I or a salt thereof, wherein:

$R^1$ is one of $CF_3$, $CHF_2$, and $CH_2F$;

$R^2$ is absent or is $C_1$-$C_8$ alkyl, optionally substituted with halo;

$R^3$, $R^4$, and $R^5$ are independently H or methyl;

G is one of —CH=CH—NHC(O)—$R^6$, —CH=CH—NHC(S)—$R^6$, —$CH_2CH_2$NHC(O)—$R^6$, —$CH_2CH_2$NHC(S)—$R^6$, —$CH_2$NHNHC(O)—$R^6$, or —$CH_2$NHNHC(S)—$R^6$;

$R^6$ is one of $C_1$-$C_6$ alkyl, —O($C_1$-$C_6$ alkyl), —S($C_1$-$C_6$ alkyl), or —N($R^7$)$_2$; and each $R^7$ is independently H or —$C_1$-$C_6$ alkyl.

2. The compound of claim 1, or a salt thereof, wherein $R^2$ is $C_1$-$C_8$ alkyl, optionally substituted with halo.

3. The compound of claim 1, or a salt thereof, wherein $R^1$ is $CF_3$.

4. The compound of claim 1, or a salt thereof, wherein $R^1$ is $CHF_2$.

5. The compound of claim 1, or a salt thereof, wherein $R^1$ is $CH_2F$.

6. The compound of claim 1, or a salt thereof, wherein G is —CH=CH—NHC(O)—$R^6$.

7. The compound of claim 1, or a salt thereof, wherein G is —CH=CH—NHC(S)—$R^6$.

8. The compound of claim 1, or a salt thereof, wherein G is —$CH_2CH_2$NHC(O)—$R^6$.

9. The compound of claim 1, or a salt thereof, wherein G is —$CH_2CH_2$NHC(S)—$R^6$.

10. The compound of claim 1, or a salt thereof, wherein G is —$CH_2$NHNHC(O)—$R^6$.

11. The compound of claim 1, or a salt thereof, wherein G is —$CH_2$NHNHC(S)—$R^6$.

12. A compound of formula 1, 2, 3, 4, 5, 6, 7, 8, 9, 10, 11, 12, 13, 14, 15, or 16:

1

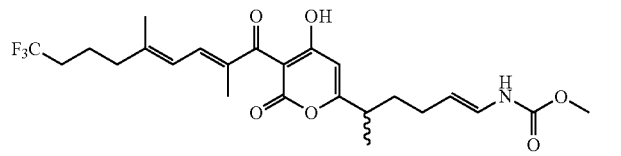

2

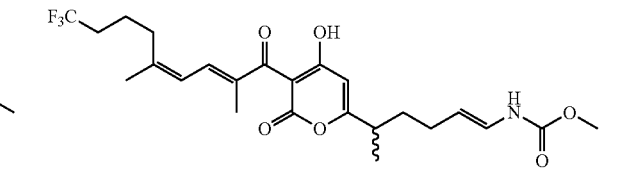

3

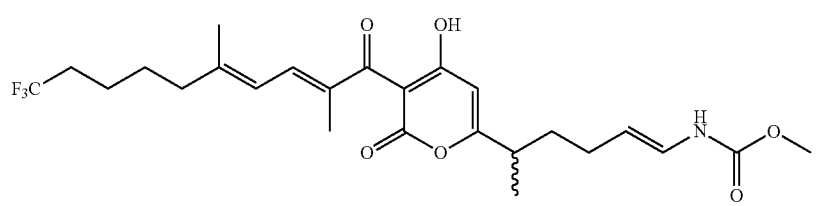

4

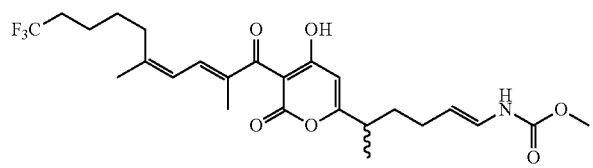

5

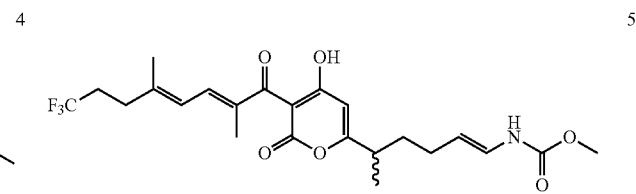

-continued
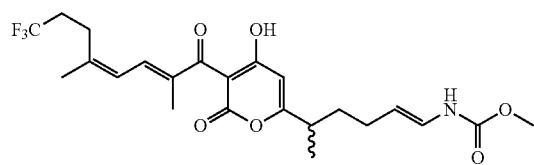
6
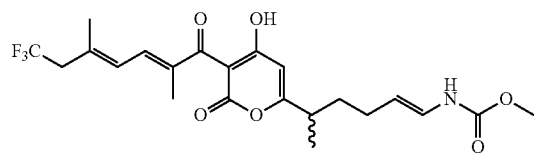
7
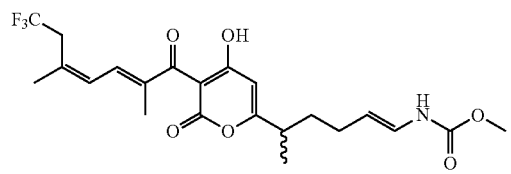
8
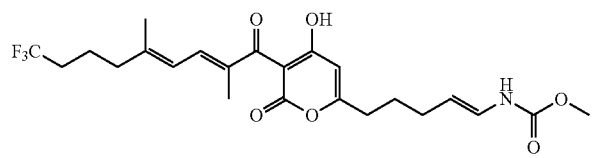
9
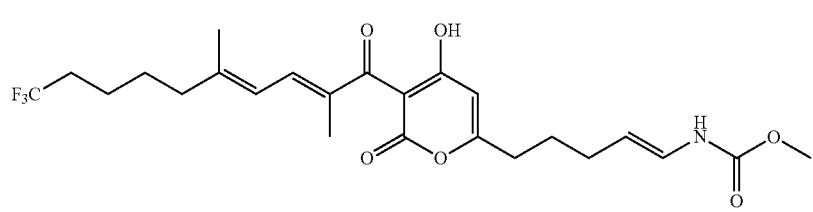
10
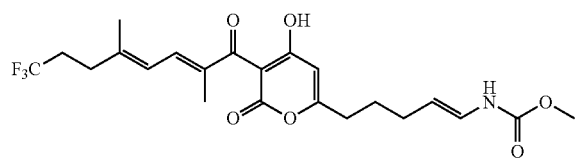
11
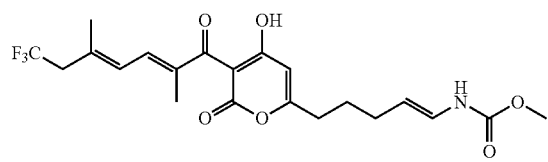
12
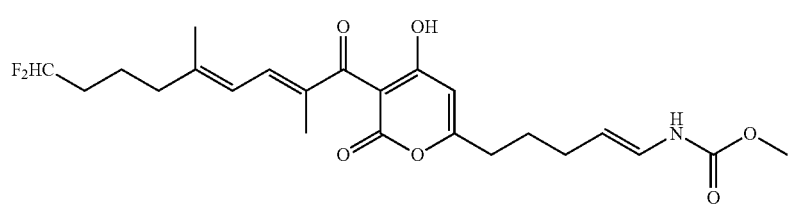
13
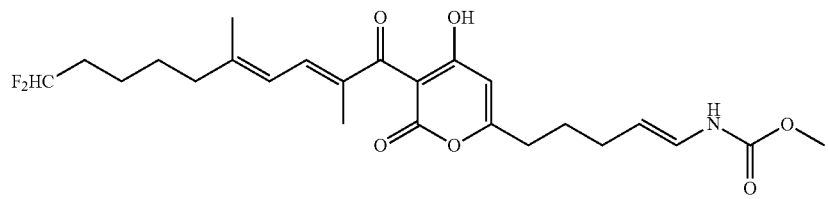
14

15
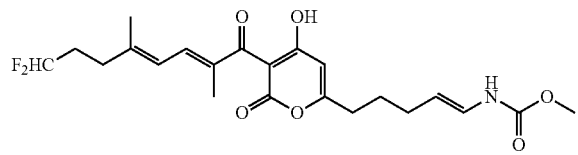

16
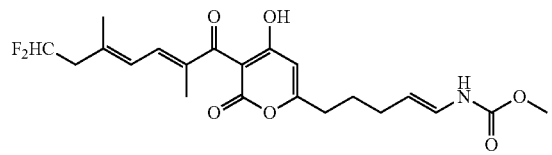

or a salt thereof.

13. The compound of claim 1, or a salt thereof, wherein the salt is a pharmaceutically acceptable salt.

14. A pharmaceutical composition comprising a compound of claim 1, or a salt thereof, and a pharmaceutically acceptable carrier.

15. A method of inhibiting a bacterial RNAP, comprising contacting a bacterial RNAP with a compound of claim 1, or a salt thereof.

16. A method of treating a bacterial infection in a mammal, comprising administering to the mammal a therapeutically effective amount of a compound of claim 1, or a salt thereof.

17. The method of claim 15, wherein the bacterium is *Mycobacterium* sp., *Staphylococcus* sp., *Enterococcus* sp., *Bacillus* sp., *Escherichia* sp., *Francisella* sp., *Burkholderia* sp., or *Brucella* sp.

18. A composition comprising:
(a) from about 0.1 mg/ml to about 10 mg/ml of a compound of claim 1, or a pharmaceutically acceptable salt thereof;
(b) from about 0% to about 10% dimethylacetamide; and
(c) from about 0% to about 8% Cremophor EL;
and having a pH of at least about 6.

19. The composition of claim 18 that comprises from about 0.6 mg/ml to about 6 mg/ml of claim 1, or a pharmaceutically acceptable salt thereof; about 0% to about 7.5% dimethylacetamide; and about 0% to about 6% Cremophor EL; and that has a pH of at least about 7.

20. The composition of claim 18 that comprises about 3 mg/ml of the compound of claim 1, or a pharmaceutically acceptable salt thereof; about 5% dimethylacetamide; and about 4% Cremophor EL; and that has a pH of about 7.4.

* * * * *